(12) United States Patent
St. Pierre et al.

(10) Patent No.: US 11,000,241 B2
(45) Date of Patent: May 11, 2021

(54) BREAST SECUREMENT DEVICES AND METHODS OF SECURING BREASTS FOR IMAGING

(71) Applicant: Hologic, Inc., Marlborough, MA (US)

(72) Inventors: Shawn St. Pierre, New Milford, CT (US); Timothy R. Stango, Sandy Hook, CT (US); Christopher Marvel, Beacon, NY (US)

(73) Assignee: Hologic, Inc., Marlborough, MA (US)

( * ) Notice: Subject to any disclaimer, the term of this patent is extended or adjusted under 35 U.S.C. 154(b) by 0 days.

(21) Appl. No.: 16/577,541

(22) Filed: Sep. 20, 2019

(65) Prior Publication Data

US 2020/0093193 A1     Mar. 26, 2020

Related U.S. Application Data

(60) Provisional application No. 62/734,795, filed on Sep. 21, 2018.

(51) Int. Cl.
| | |
|---|---|
| *A61B 6/04* | (2006.01) |
| *A41C 3/00* | (2006.01) |
| *A61B 6/00* | (2006.01) |

(52) U.S. Cl.
CPC .......... *A61B 6/0421* (2013.01); *A41C 3/0064* (2013.01); *A61B 6/0492* (2013.01); *A61B 6/502* (2013.01)

(58) Field of Classification Search
None
See application file for complete search history.

(56) References Cited

U.S. PATENT DOCUMENTS

| | | | | | |
|---|---|---|---|---|---|
| 6,589,254 | B2 * | 7/2003 | Fontenot | ................ | A61B 90/17 600/231 |
| 6,846,218 | B2 * | 1/2005 | Kermode | .............. | A61F 13/145 450/37 |
| 6,987,831 | B2 * | 1/2006 | Ning | ...................... | A61B 6/032 378/20 |
| 7,697,660 | B2 * | 4/2010 | Ning | ...................... | A61B 6/466 378/37 |
| 7,699,783 | B2 * | 4/2010 | Hanover | ................ | A61B 8/406 600/459 |
| 7,771,360 | B2 * | 8/2010 | Johnson | ............... | A61B 8/4209 600/459 |
| 8,515,525 | B2 * | 8/2013 | DeRobertis | ............ | A61B 6/502 600/415 |
| 8,787,522 | B2 * | 7/2014 | Smith | ................... | A61B 6/027 378/37 |

(Continued)

*Primary Examiner* — Thomas R Artman

(57) ABSTRACT

A breast securement device for an imaging system is provided. The securement device includes a retainer configured to attach to at least a portion of a patient's breast and a tensioning system coupled to the retainer. The tensioning system is configured to pull the retainer away from a chest wall of the patient so as to apply a pulling force to the patient's breast. The retainer may include a substantially tubular-shaped mesh material having a first end configured to receive at least a portion of the patient's breast and an opposite second end coupled to the tensioning system. In another example, the retainer may include a vacuum bag having a first end configured to receive at least a portion of the patient's breast. In still another example, the retainer may include an adhesive member configured to adhere to the patient's breast.

17 Claims, 11 Drawing Sheets

(56) References Cited

U.S. PATENT DOCUMENTS

| | | | | |
|---|---|---|---|---|
| 8,821,573 B2* | 9/2014 | Khouri | | A61H 7/00 623/8 |
| 9,808,214 B2* | 11/2017 | Smith | | A61B 6/405 |
| 10,561,387 B2* | 2/2020 | Smith | | A61B 6/466 |
| 10,575,804 B2* | 3/2020 | Smith | | A61B 6/482 |
| 2002/0099264 A1* | 7/2002 | Fontenot | | A61B 90/11 600/130 |
| 2004/0081273 A1* | 4/2004 | Ning | | A61B 6/04 378/37 |
| 2004/0219864 A1* | 11/2004 | Kermode | | A61F 13/145 450/1 |
| 2005/0143638 A1* | 6/2005 | Johnson | | A61B 5/415 600/407 |
| 2006/0009693 A1* | 1/2006 | Hanover | | A61B 5/418 600/407 |
| 2006/0009696 A1* | 1/2006 | Hanover | | A61B 90/17 600/437 |
| 2006/0094950 A1* | 5/2006 | Ning | | A61B 6/06 600/407 |
| 2007/0276229 A1* | 11/2007 | Adler | | A61B 90/17 600/426 |
| 2009/0080602 A1* | 3/2009 | Brooks | | A61B 6/502 378/20 |
| 2010/0140500 A1* | 6/2010 | Jesseph | | A61N 5/10 250/454.11 |
| 2012/0016223 A1* | 1/2012 | DeRobertis | | A61B 6/502 600/407 |
| 2012/0114095 A1* | 5/2012 | Smith | | A61B 6/482 378/20 |
| 2013/0046383 A1* | 2/2013 | Khouri | | A61F 2/12 623/8 |
| 2014/0321607 A1* | 10/2014 | Smith | | A61B 6/032 378/16 |
| 2017/0086765 A1* | 3/2017 | Smith | | A61B 6/0414 |
| 2017/0120078 A1* | 5/2017 | Payne | | A61B 8/406 |
| 2017/0325767 A9* | 11/2017 | Smith | | A61B 6/025 |
| 2018/0035963 A1* | 2/2018 | Smith | | A61B 6/463 |
| 2020/0093193 A1* | 3/2020 | St. Pierre | | A61B 6/502 |
| 2020/0146644 A1* | 5/2020 | Smith | | A61B 6/0414 |

* cited by examiner

BREAST SECUREMENT DEVICES AND METHODS OF SECURING BREASTS FOR IMAGING

CROSS-REFERENCE TO RELATED APPLICATIONS

This application claims priority to and the benefit of U.S. Provisional Patent Application No. 62/734,795, filed Sep. 21, 2018, the disclosure of which is hereby incorporated by reference herein in its entirety.

BACKGROUND

Breast securement during medical imaging (e.g., screening and diagnostic imaging procedures) serves a number of purposes. For example, it substantially stabilizes the breast during the imaging procedures, and thereby, reduces breast movement and image blurring. Additionally, optimal breast securement brings breast tissue out from the chest wall into the imaging field, and thus, enables more tissue imaging.

Some known breast securement methods include compressing and immobilizing the patient's breast for mammography, tomosynthesis, and/or computer tomography (CT) imaging. These systems generally use a movable, rigid, radiolucent compression paddle. The patient's breast is placed in an imaging area on a breast support platform that typically is flat, and the paddle then compresses the breast, usually while a technologist or other health professional is holding the breast in place. The technologist may also manipulate the breast to try to get proper tissue coverage in the image field.

One known challenge in breast stabilization is the discomfort the patient may feel when the breast is secured, which must be done with sufficient force to stabilize the breast. Discomfort may potentially cause the patient to move, which negatively impacts image quality. Discomfort may also potentially dissuade patients from getting screened for breast cancer. Another known challenge is to ensure that the imaged field includes the desired amount of breast tissue as stabilization may push breast tissue towards the patient's chest wall. Furthermore, the breast securement devices need to reduce or eliminate image artifacts being formed in the image.

SUMMARY

In one aspect, the technology relates to a breast securement device for an imaging system, the securement device including: a retainer configured to attach to at least a portion of a patient's breast; and a tensioning system coupled to the retainer, wherein the tensioning system is configured to pull the retainer away from a chest wall of the patient so as to apply a pulling force to the patient's breast.

In an example, the retainer includes a substantially tubular-shaped mesh material having a first end configured to receive at least a portion of the patient's breast and an opposite second end coupled to the tensioning system, and when tension is applied to the mesh material, the mesh material tightens at least partially around the patient's breast. In another example, the mesh material includes an inner surface, and wherein at least a portion of the inner surface is coated with a silicone-based material so as to increase a grip on the patient's breast. In still another example, the mesh material includes a substantially cylindrical, helically wound braid.

In another example, the retainer includes a vacuum bag having a first end configured to receive at least a portion of the patient's breast, and the vacuum bag is coupled to a vacuum line so as to capture at least a portion of breast tissue within the vacuum bag. In still another example, the vacuum line is removably coupled to the vacuum bag. In yet another example, the first end of the vacuum bag is configured to generate a seal at the patient's chest wall. In an example, the vacuum bag includes a second end removably coupled to the tensioning system.

In still another example, the retainer includes an adhesive member configured to adhere to the patient's breast, and the adhesive member is removably coupled to the tensioning system. In yet another example, the adhesive member includes a foam and/or a pad. In an example, a bra includes the adhesive member. In another example, the retainer includes one or more markers.

In another aspect, the technology relates to a method of securing a patient's breast for imaging, the method including: attaching a retainer to at least a portion of the patient's breast; and pulling the retainer away from a chest wall of the patient.

In an example, attaching the retainer includes inserting at least a portion of the patient's breast into a first end of a substantially tubular-shaped mesh material. In another example, attaching the retainer includes: inserting at least a portion of the patient's breast into a first end of a vacuum bag; and creating a suction in the vacuum bag to capture breast tissue within the vacuum bag. In still another example, the method further includes coupling a vacuum line to the vacuum bag. In yet another example, the method further includes coupling a second end of the vacuum bag to a tensioning system. In an example, attaching the retainer includes adhering an adhesive member to the patient's breast. In another example, a bra includes the adhesive member, and the method further includes attaching the bra to the patient. In still another example, the method includes positioning the patient's beast on an imaging system based at least in part by a location of one or more markers disposed on the retainer relative to the imaging system.

In another aspect, the technology relates to a breast liner for an imaging system, the breast liner including: an adhesive layer; and at least one marker configured to position a patient's breast relative to at least a portion of the imaging system. In an example, the at least one marker is based on a previously identified region of interest. In another example, the at least one maker includes a grid pattern.

In still another aspect, the technology relates to a method of imaging a patient's beast in an imaging system, the method including: adhering a breast liner to at least a portion of the patient's breast, wherein the breast liner includes at least one marker; and positioning the patient's breast on the imaging system based at least in part by a location of at least one marker relative to the imaging system. In an example, the method further includes printing the breast liner with the at least one marker corresponding to a previously identified region of interest. In another example, the method further includes adjusting the patient's breast on the imaging system based on the at least one marker.

In yet another aspect, the technology relates to an imaging system including: a bra configured to stabilize a patient's breast; an imaging source; and a detector, wherein the imaging source and the detector are selectively positionable relative to the bra for breast imaging. In an example, the imaging system further includes an intensifier. In another example, an articulator supporting the imaging source and the detector is included, the articulator configured to position the imaging source and/or the detector at any location around the patient's breast. In still another example, the bra is radiolucent.

In another aspect, the technology relates to a method of imaging a patient's breast, the method including: attaching a bra to a patent; and imaging the patient's breast via an imaging system that is selectively positionable relative to the bra. In an example, the method further includes articulating the imaging system to any location around the patient's breast.

DETAILED DESCRIPTION

Figure 1A:
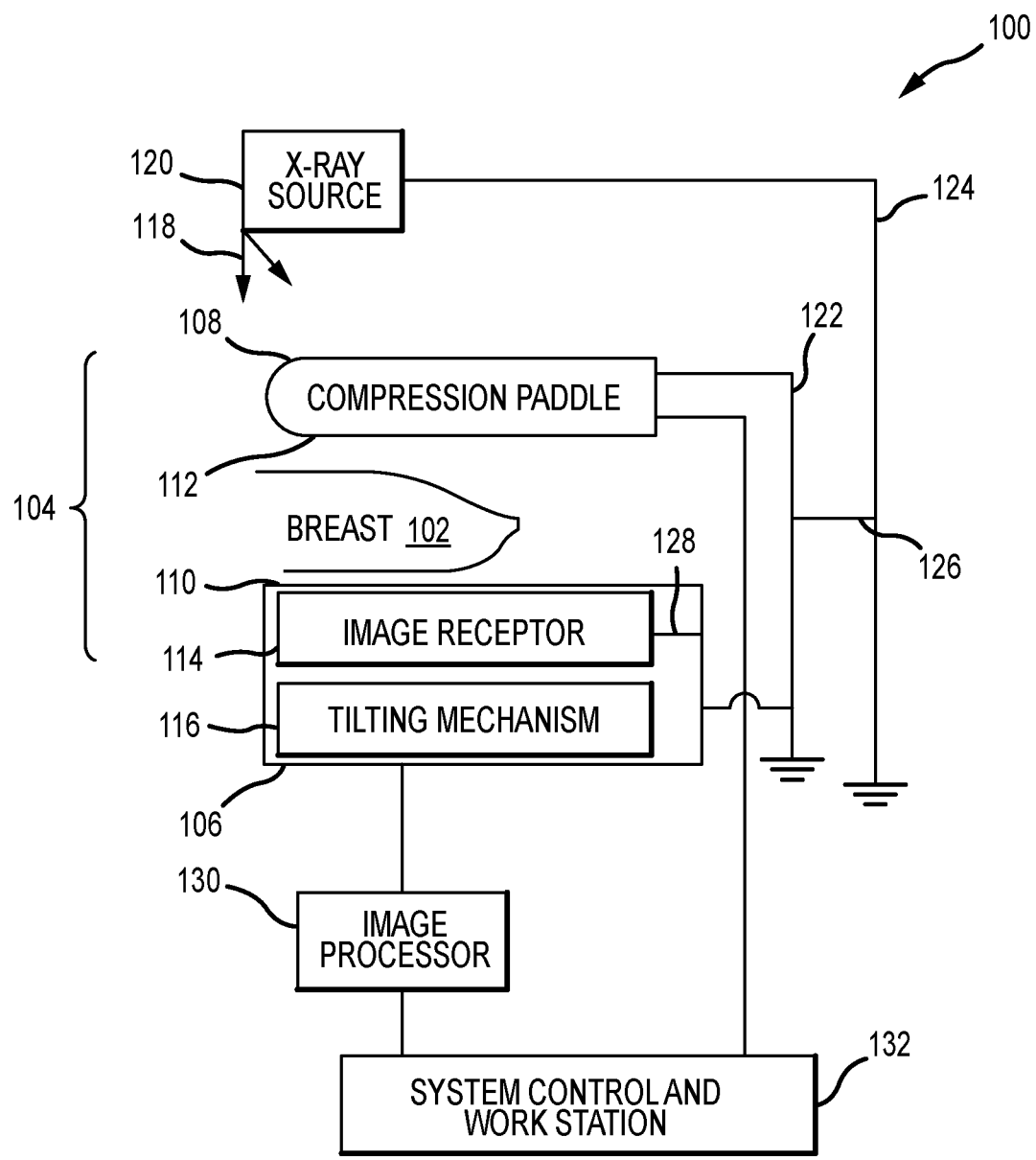
FIG. 1A is a schematic view of an exemplary imaging system.
Figure 1B:
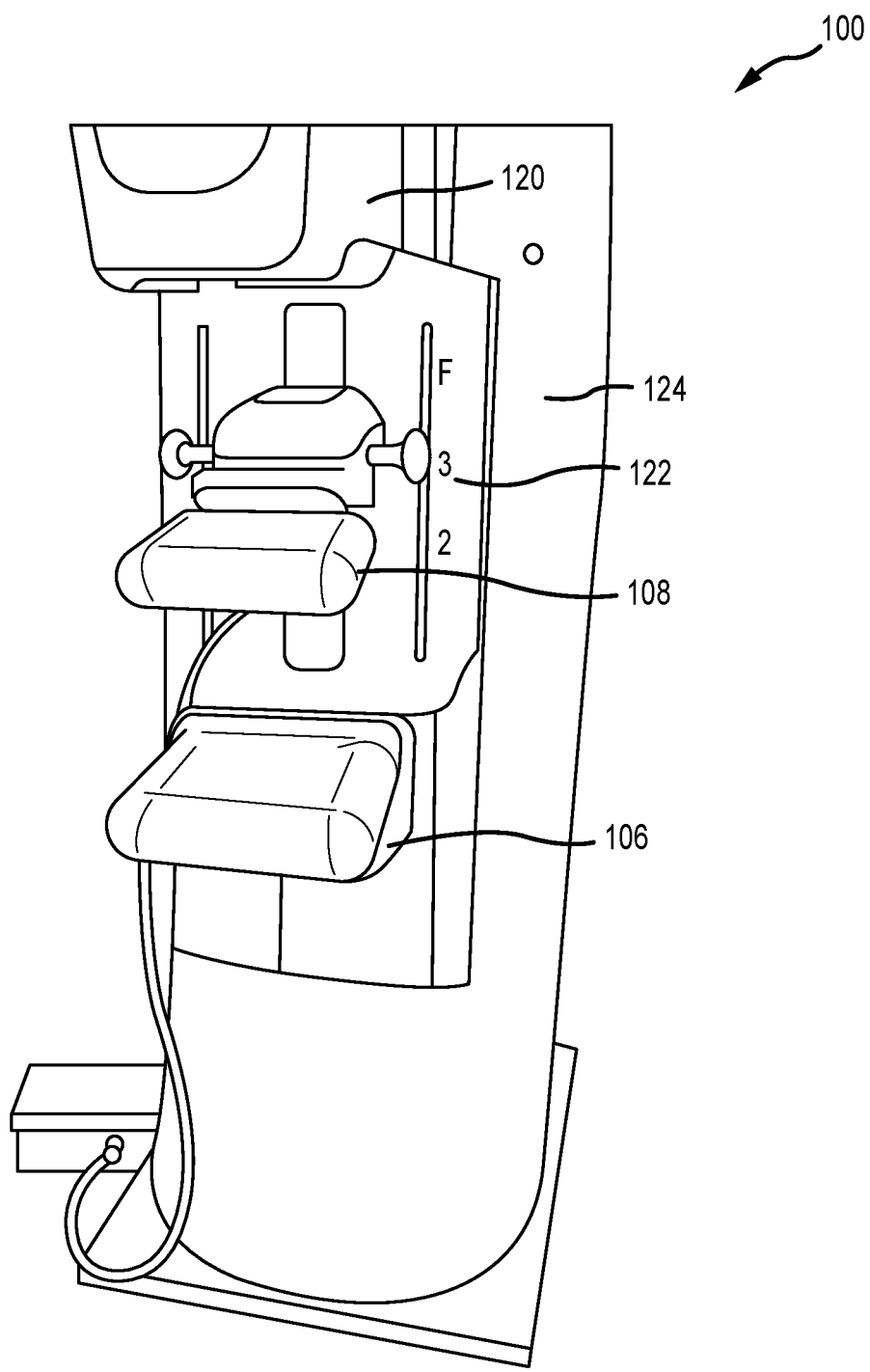
FIG. 1B is a perspective view of the imaging system of FIG. 1A.

FIG. 1A is a schematic view of an exemplary imaging system 100. FIG. 1B is a perspective view of the imaging system 100. Referring concurrently to FIGS. 1A and 1B, the imaging system 100 is configured to compress a patient's breast 102 for x-ray imaging via a breast compression system 104. In the example, the compression system 104 includes a breast support platform 106 and a moveable compression paddle 108. The breast support platform 106 and the compression paddle 108 each have a compression surface 110 and 112, respectively, with the compression surface 112 configured to move towards the support platform 106 to compress the breast 102 therebetween. In known systems, the compression surfaces 110, 112 are exposed so as to directly contact the breast 102. The support platform 106 also houses an image receptor 114 and, optionally, a tilting mechanism 116. The compression system 104 is in a path of an imaging x-ray beam 118 emanating from an x-ray source 120, such that the beam 118 impinges on the image receptor 114.

The compression system 104 is supported on a first support arm 122 and the x-ray source 120 is supported on a second support arm, also referred to as a tube arm 124. For mammography, support arms 122 and 124 can rotate as a unit about an axis 126 between different imaging orientations such as cranial-caudal (CC) and mediolateral oblique (MLO) views, so that the imaging system 100 can take a mammogram projection image at each orientation. In operation, the image receptor 114 remains in place relative to the support platform 106 while an image is taken. The compression system 104 releases the breast 102 for movement of support arms 122, 124 to a different imaging orientation. For tomosynthesis, the support arm 122 stays in place, with the breast 102 compressed and remaining in place, while at least the tube arm 124 rotates the x-ray source 120 relative to the compression system 104 and the compressed breast 102 about the axis 126. The imaging system 100 takes plural tomosynthesis projection images of the breast 102 at respective angles of the x-ray beam 118 relative to the breast 102. As such, the compression system 104 and tube arm 124 may be rotated discrete from each other, unless matched rotation is required or desired for an imaging procedure.

Concurrently and optionally, the image receptor 114 may be tilted relative to the breast support platform 106 and coordinated with the rotation of the second support arm 124. The tilting can be through the same angle as the rotation of the x-ray source 120, but may also be through a different angle selected such that the x-ray beam 118 remains substantially in the same position on the image receptor 114 for each of the plural images. The tilting can be about an axis 128, which can but need not be in the image plane of the image receptor 114. The tilting mechanism 116 that is coupled to the image receptor 114 can drive the image receptor 114 in a tilting motion. For tomosynthesis imaging and/or CT imaging, the breast support platform 106 can be horizontal or can be at an angle to the horizontal, e.g., at an orientation similar to that for conventional MLO imaging in mammography. The imaging system 100 can be solely a mammography system, a CT system, or solely a tomosynthesis system, or a "combo" system that can perform multiple forms of imaging. An example of one combo system has been offered by the assignee hereof under the trade name Selenia Dimensions. For CT systems, the breast 102 may be compressed in the compression system 104, however, the image receptor 114 is remote from the support platform 106 and rotates with the x-ray source 120 and relative to the compression system 104.

When the system is operated, the image receptor 114 produces imaging information in response to illumination by the imaging x-ray beam 118, and supplies it to an image processor 130 for processing and generating breast x-ray images. A system control and work station unit 132, including software, controls the operation of the system and interacts with the operator to receive commands and deliver information including processed-ray images.

While the imaging system 100 described above is an x-ray imaging system, it should be appreciated that the imaging system 100 can alternatively or additionally be any other type of imaging system as required or desired. In one example, the imaging system 100 may be an ultrasound imaging system that generates ultrasonic images of the patient's breast 102 via sound waves. In another example, the imaging system 100 may be a magnetic resonance imaging (MRI) system that generates images of the patient's breast 102 via radio waves. Other imaging systems known in breast diagnosis and screening procedures are also contemplated herein. In each example of the imaging system 100, it is desirable to sufficiently secure the patient's breast 102 so as to reduce breast movement and image blurring. Shaping the patient's breast 102 may also be desirable so as to increase imaging procedure efficiencies. Additionally, breast securement and/or shaping can bring breast tissue out from the chest wall into the imaging field, and thus, enabling greater tissue imaging.

One challenge in each example of the imaging system 100 (e.g., mammography, tomosynthesis, CT, ultrasound, MM, etc.) is how to efficiently secure the breast 102 for the desired or required imaging. In each example, it is desirable to sufficiently secure the patient's breast 102 so as to reduce breast movement and image blurring during image acquisition. Additionally, breast securement can shape the breast 102 while also bringing breast tissue out from the chest wall into the imaging field. Thus, breast stabilization and shaping enables more effective and efficient breast tissue imaging. Furthermore, breast securement increases patient comfort, which further reduces patient movement. Other benefits may also be realized by securing and stabilizing the patient's breast.

The technologies described herein relate to securement devices and methods that are configured to stabilize the patient's breast 102 with respect to the imaging system 100, without requiring the compression pressure typical of that in the compression system 104 that is described above. Unlike the typical hard plastic compression paddles 108, the securement devices herein need not flatten the breast 102. Rather, the securement devices are used to stabilize and/or shape the patient's breast 102, not necessarily to effectuate full compression. Additionally, the securement devices may be used prior to full compression and flattening, for example, to adjust the patient's breast 102 within the compression system 104. Accordingly, as described herein, breast securing sufficiently stabilizes the patient's breast with respect to the imaging system 100 such that movement of the breast is restricted or eliminated. This breast securing and stabilization may not result in full compression and flattening, but may reduce or eliminate image blurring, while increasing the efficiency, comfort, and performance of the imaging procedure. Exemplary breast securement devices and methods are described in further detail below.

The wearable breast securement devices and methods described herein are configured to stabilize and/or shape the patient's breast with respect to an imaging system. As such, the patient's breast is restricted or prevented from moving during imaging procedures to reduce or eliminate image blurring, while increasing the efficiency, comfort, and performance of the imaging procedure. The breast securement devices are also substantially radiolucent and/or sonolucent to reduce image artifacts being formed in the image. In an aspect, a mesh material is configured to tighten around the patient's breast as the mesh material is drawn away from the patient's chest wall. The mesh material is easy to position around the patient's breast for patient comfort, while enabling stabilization and/or shaping of the breast for imaging because of the tightening functionality. Additionally, the pulling of the mesh material pulls breast tissue away from the chest wall, thereby increasing imaging efficiencies. In another aspect, a vacuum bag is configured to capture the patient's breast and be utilized to draw the breast away from the chest wall. The vacuum bag is also easy to position around the patient's breast for comfort, while enabling stabilization and/or shaping of the breast for imaging. Additionally, the pulling of the vacuum bag pulls breast tissue away from the chest wall, thereby increasing imaging efficiencies. In yet another aspect, an adhesive member is configured to adhere to the patient's breast and be utilized to draw the breast away from the chest wall. The adhesive member is also easy to position around the patient's breast for comfort, while enabling stabilization and/or shaping of the breast for imaging. Additionally, the pulling of the adhesive member pulls breast tissue away from the chest wall, thereby increasing imaging efficiencies. These devices enable the stabilization and/or shaping the patient's breast for imaging, without requiring the compression pressure typical in breast imaging systems.

In other examples, the patient's breast may be stabilized and/or shaped by a radiolucent bra. In this example, instead of moving the patient and positioning the bra on the imaging system, the imaging system can be positioned and moved relative to the bra by an actuator for imaging procedures. This enables the patient to be in a more comfortable position for imaging. Additionally, the bra restricts or prevents breast tissue from moving during imaging to reduce or eliminate image blurring, while increasing the efficiency, comfort, and performance of the imaging procedure.

Additionally or alternatively, wearable position markers may be included in the devices described above, or on their own in a separate breast liner adhered to at least a portion of the patient's breast. These markers can be radio-opaque such that the imaging source can be used to facilitate positioning the patient's breast, or may be radiolucent such that the markers reduce or eliminate image artifacts in the breast image. In either case, the markers can be used by the technologist to more efficiently position the patient's breast on the imaging system, thereby increasing imaging procedure efficiencies. In some examples, the markers may correspond to a predetermined region of interest so that the technologist can more efficiently position and orient the region of interest in the image area of the imaging system.

Figure 2:
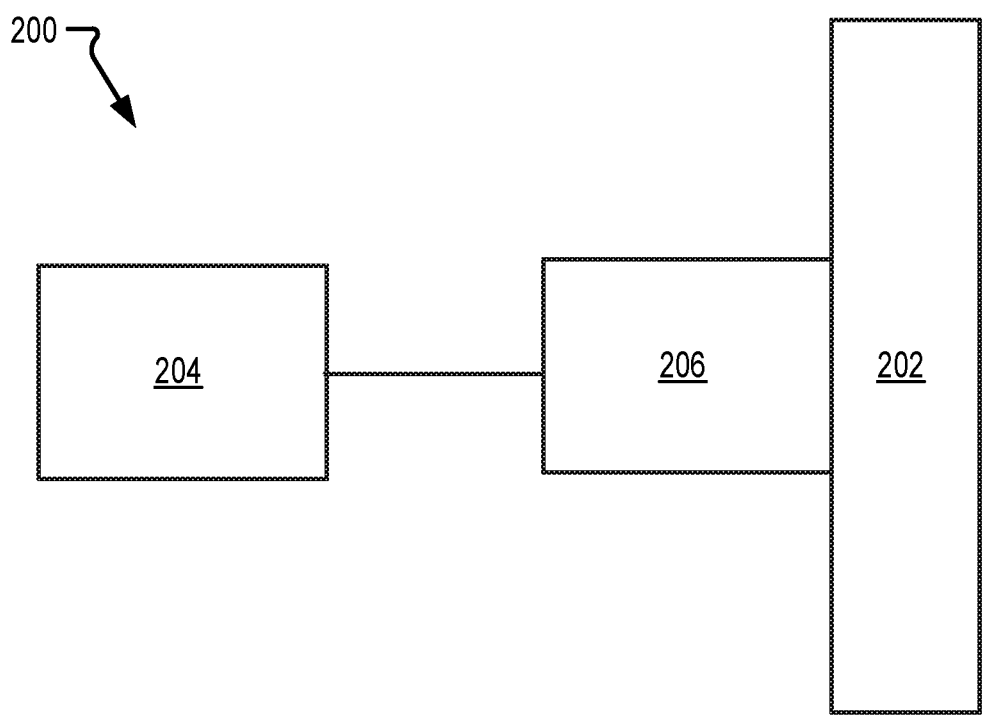
FIG. 2 is a schematic view of an exemplary breast securement device.

FIG. 2 is a schematic view of an exemplary breast securement device 200. The breast securement device 200 is configured to operationally couple to an imaging system 202 (e.g., mammography, tomosynthesis, CT, ultrasound, MM, etc.) and stabilize and/or shape the patient's breast. The breast securement device 200 includes a retainer 204 that is configured to attach to at least a portion of the patient's breast. In some examples, the retainer 204 may also at least partially shape the patient's breast so as to increase imaging efficiencies. The retainer 204 is operationally coupled to a tensioning system 206. The tensioning system 206 is configured to pull the retainer 204 away from a chest wall of the patient so as to apply a pulling force to the patient's breast. This pulling force stabilizes the patient's breast such that the breast does not move during imaging and the patient's comfort is increased. In some examples, the tensioning system 206 may be coupled to one of the support arms 122 and 124 (shown in FIG. 1A) so as to assist with the placement of the patient's breast within an imaging area of the imaging system 202. More detailed examples of the breast securement device 200 are described with reference to FIGS. 3-6 below.

Figure 3:
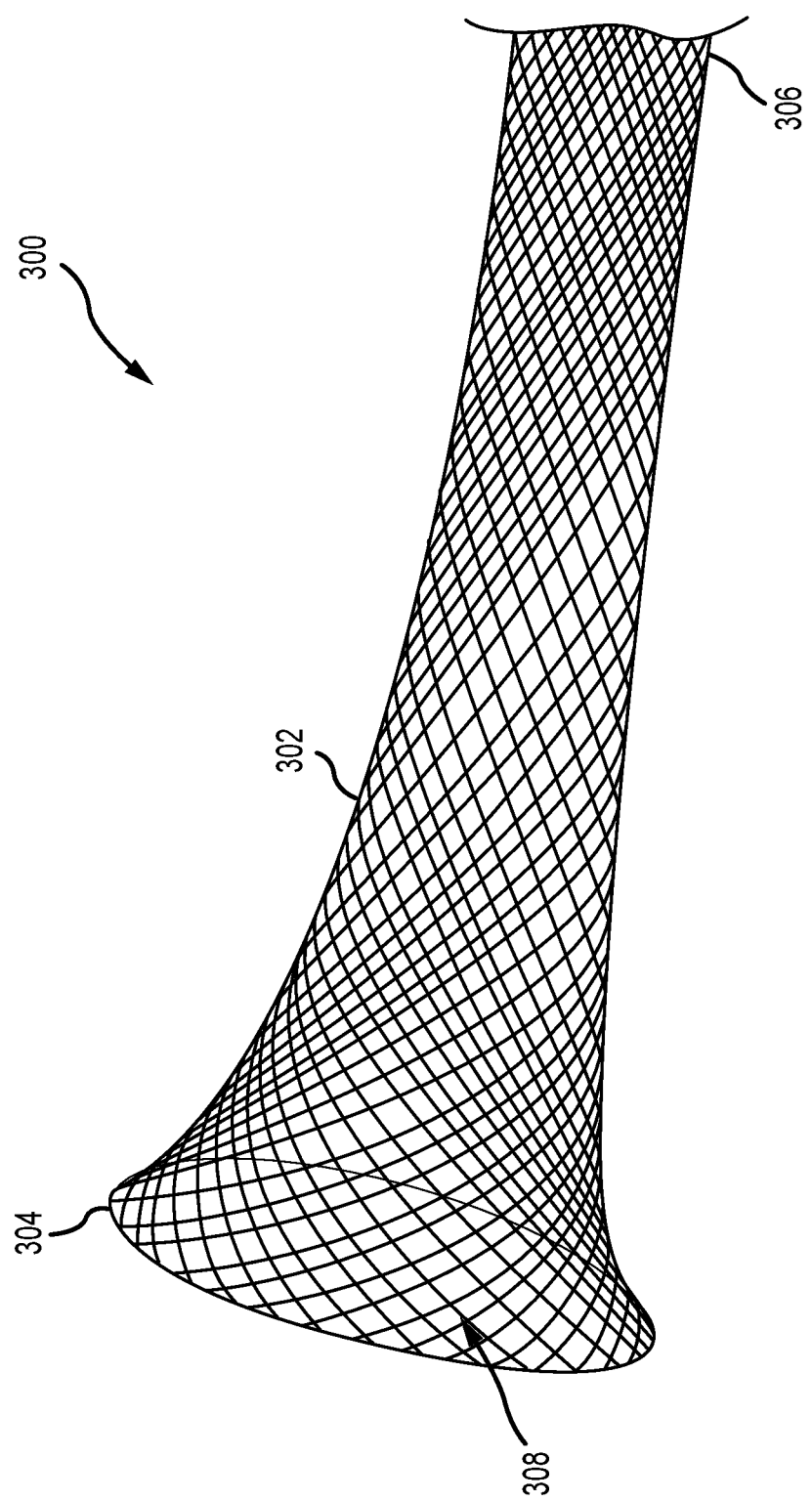
FIG. 3 is a perspective view of an exemplary retainer for use with the breast securement device of FIG. 2.

FIG. 3 is a perspective view of an exemplary retainer 300 for use with the breast securement device 200 (shown in FIG. 2). In the example, the retainer 300 includes a substantially tubular-shaped mesh material 302 having a first end 304 and an opposite second end 306. The first end 304 is open and is configured to receive at least a portion of the patient's breast therein. The second end 306 is coupled to the tensioning system 206 (shown in FIG. 2) such that when tension is applied to the mesh material 302, it tightens at least partially around the patient's breast. This tightening enables the breast to be stabilized relative to the imaging system and the tensioning enables the breast tissue to be pulled away from the patient's chest wall. To loosen the retainer 300, the mesh material 302 can be released from tension to remove the first end 304 from the patient's breast.

In the example, the mesh material 302 may be a substantially cylindrical, helically wound braid (for example, a biaxial braid). As such, pulling the entire braid lengthens and narrows it, and the more tension is applied, the more the circumference of the material 302 reduces around the patient's breast. In some examples, an inner surface 308 of the mesh material 302 may be at least partially coated with a silicone-based material so as to further increase grip about the patient's breast. Additionally or alternatively, the mesh material 302 may include one or more markers that are utilized to assist in positioning the patient's breast relative to the imaging system.

Figure 4:
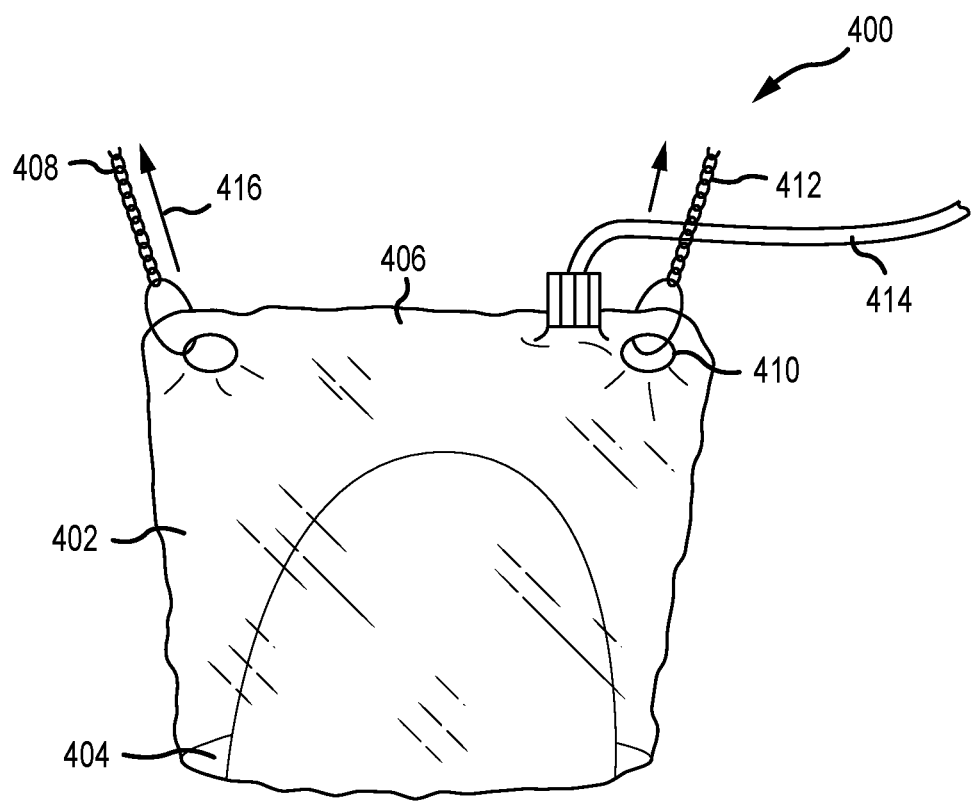
FIG. 4 is a top view of another retainer for use with the breast securement device of FIG. 2.

FIG. 4 is a top view of another retainer 400 for use with the breast securement device 200 (shown in FIG. 2). In this example, the retainer includes a vacuum bag 402 having a first end 404 and an opposite second end 406. The first end 404 includes a recess that is configured to receive at least a portion of the patient's breast. The second end 406 is removably coupled to a tensioning system 408. For example, the second end 406 includes one or more holes 410 that can be reinforced with a grommet and the tensioning system 408 can include one or more chains 412 that are selectively attachable to the holes 410. Other types of connection systems may also be used as required or desired.

In operation, the first end 404 of the vacuum bag 402 is placed around the patient's breast, and the bag 402 is removably coupled (e.g., a quick connect connection or the like) to a vacuum line 414. The vacuum line 414 is configured to create a suction in the vacuum bag 402 so as to capture breast tissue therein. The vacuum bag 402, with the breast tissue, may then be pulled 416 away from the chest wall of the patient and stabilize the breast relative to the imaging system. In some examples, the first end 404 may generate a seal at the patient's chest wall. In other examples, the vacuum bag 402 may include a plastic plate (not shown) that is configured to at least partially support and/or shape the patient's breast from below for stabilization. Since the vacuum bag 402 can be selectively attached to the image system for suction, the vacuum bag 402 can be a patient wearable component that enables the patient to put on the bag 402 before the imaging procedure. This allows the patient time to adjust and pre-position the bag 402 to fit prior to entering the screening room, thereby increasing patient comfort. The technologist then may assist the patient and make fine adjustments of the vacuum bag 402 as needed before drawing the vacuum and attaching the bag 42 to the tensioning system 408. Additionally or alternatively, the vacuum bag 402 may include one or more markers that are utilized to assist in positioning the patient's breast relative to the imaging system.

Figure 5B:
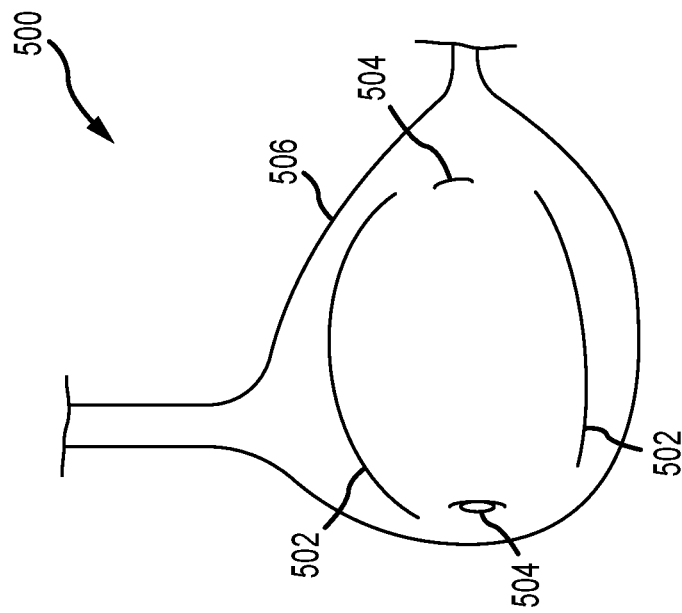
FIG. 5B is a front view of the retainer of FIG. 5A.
Figure 5A:
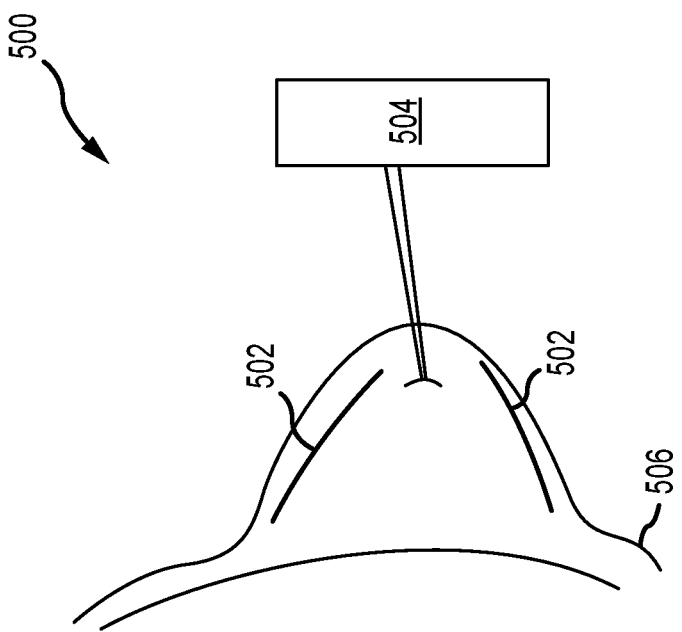
FIG. 5A is a side view of another retainer for use with the breast securement device of FIG. 2.

FIG. 5A is a side view of another retainer 500 for use with the breast securement device 200 (shown in FIG. 2). FIG. 5B is a front view of the retainer 500. Referring concurrently to FIGS. 5A and 5B, the retainer 500 includes one or more adhesive members 502 configured to adhere to the patient's breast. In one example, the adhesive member 502 may be positioned on the bottom and on the top of the patient's breast. The adhesive member 502 is removably coupled to a tensioning system 504. Because the retainer 500 is adhered to the patient's breast, the tensioning system 504 can pull on the adhesive member 502 to pull breast tissue away from the chest wall of the patient and stabilize the breast relative to the imaging system.

In this example, the adhesive members 502 may be disposed on a bra 506. The patient can wear the bra 506 for increased patient comfort. Additionally or alternatively, the adhesive member 502 may include a foam and/or pad to further increase patient comfort. The foam and/or pad may further be used to shape and form the patient's breast as required or desired for imaging. Additionally or alternatively, the adhesive members 502 may include one or more markers that are utilized to assist in positioning the patient's breast relative to the imaging system.

Figure 6:
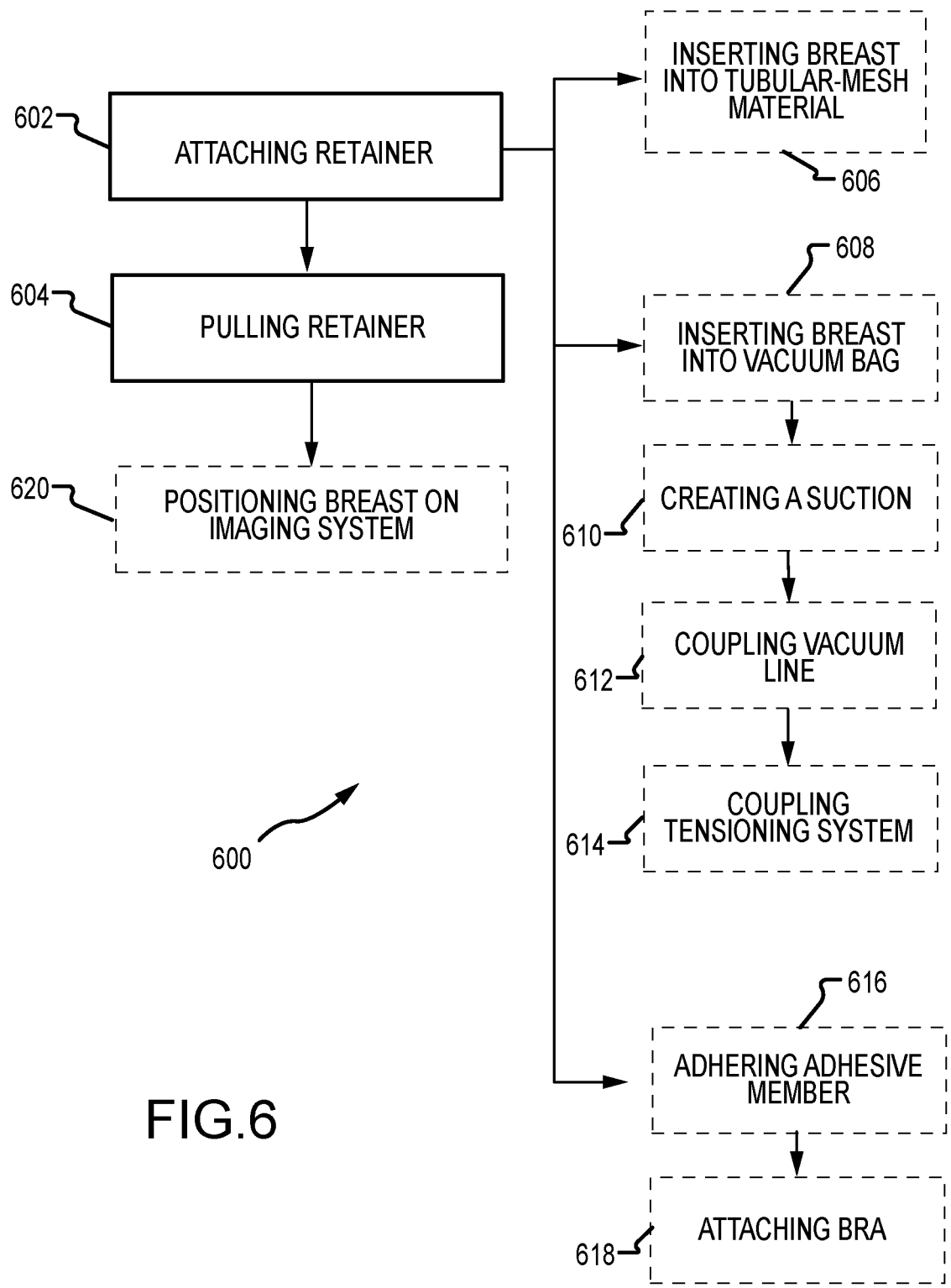
FIG. 6 is a flowchart illustrating a method of securing a patient's breast for imaging.

FIG. 6 is a flowchart illustrating a method 600 of securing a patient's breast for imaging. As described above, by sufficiently securing and stabilizing the patient's breast, breast movement and image blurring is reduced. Furthermore, breast tissue is shaped and/or pulled out from the patient's chest wall to increase efficiency of the breast tissue imaging. Patient comfort is also increased. The method 600 begins with attaching a retainer to at least a portion of the patient's breast (operation 602). The retainer is then pulled away from the patient's chest wall (operation 604). In one example, pulling the retainer away from the patient's chest wall may be performed by a tensioning element as described in reference to FIG. 2.

In one example, attaching the retainer (operation 602) may include inserting at least a portion of the patient's breast into a first end of a substantially tubular-shaped mesh material (operation 606). As described in FIG. 3, the mesh material can be tensioned so as to tightened around the patient's breast to stabilize the breast on the imaging system and to pull breast tissue away from the patient's chest wall. In another example, attaching the retainer (operation 602) may include inserting at least a portion of the patient's breast into a first end of a vacuum bag (operation 608) and creating a suction in the vacuum bag to capture breast tissue within the vacuum bag (operation 610). The vacuum bag can be coupled to a vacuum line (operation 612) and the second end of the vacuum bag can be coupled to the tensioning system (operation 614). As described in FIG. 4, the vacuum bag enables the patient to comfortably attach the bag to the breast and then approach the imaging system. Once at the imaging system, the vacuum bag seals around the breast, and thereafter, the patient's breast can be pulled away from the chest wall and stabilized on the imaging system.

In still another example, attaching the retainer (operation 602) may include adhering an adhesive member to the patient's breast (operation 616). For example, the adhesive member may be disposed on a bra such that the bra is attached to the patient (operation 618). As described in FIGS. 5A and 5B, the adhesive member can be used to pull the patient's breast away from the chest wall and stabilize on the imaging system. The method 600 may also include positioning the patient's beast on an imaging system based at least in part by a location of one or more markers disposed on the retainer relative to the imaging system (operation 620). By including positioning markers, the technologist may more easily position the patient's breast on the imaging system.

Figure 7B:
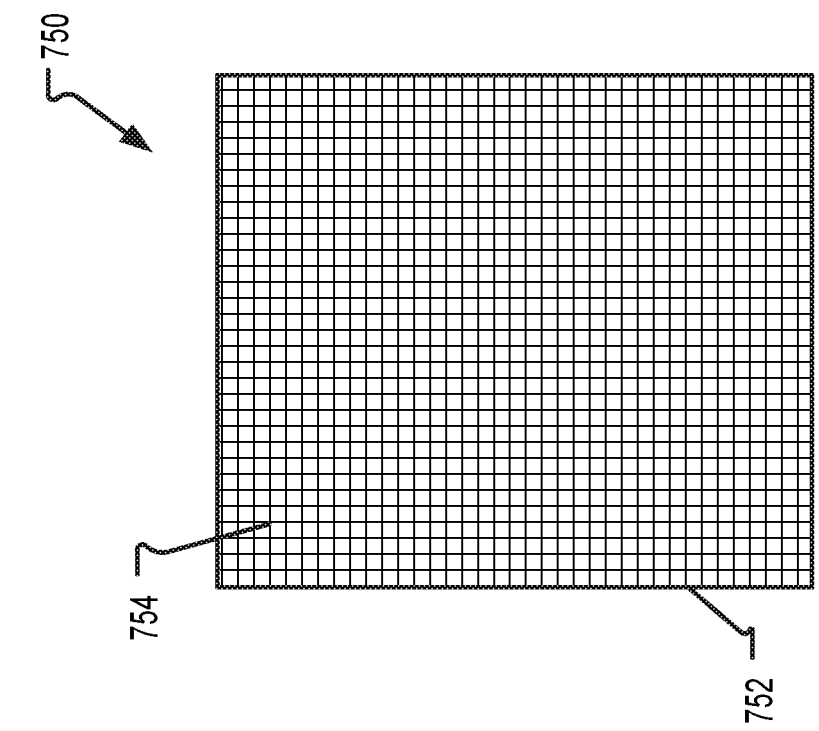
FIG. 7B is a top view of another breast liner.
Figure 7A:
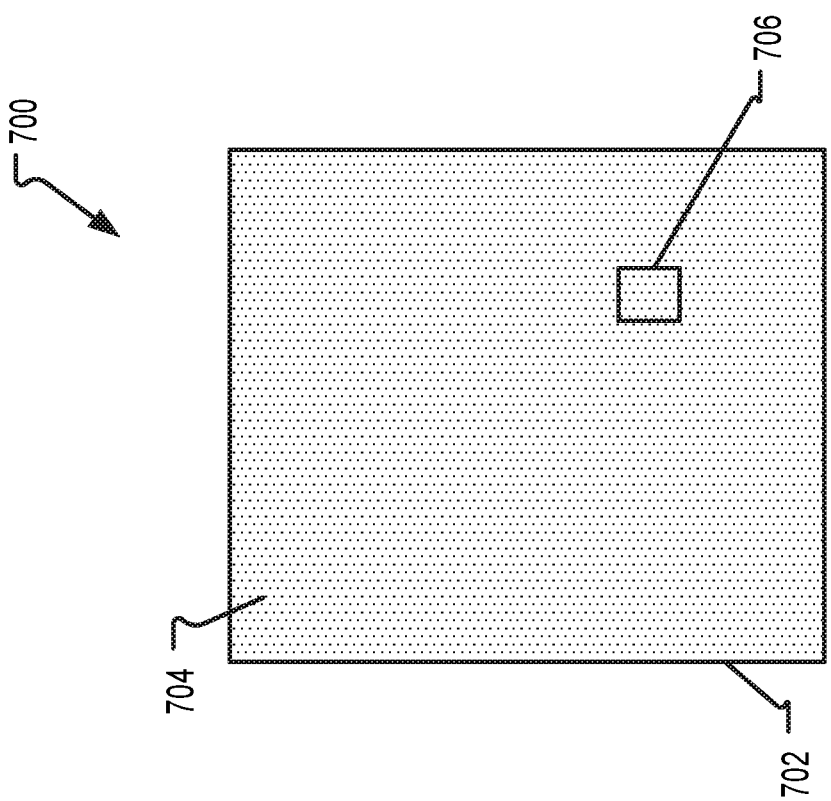
FIG. 7A is a top view of an exemplary breast liner.

FIG. 7A is a top view of an exemplary breast liner 700. The breast liner 700 can be applied to the patient's breast and facilitate positioning the breast relative to at least a portion of the imaging system. In the example, the breast liner 700 includes an adhesive layer 702 that includes at least one marker 704. The markers 704 can be utilized by the technologist to align the patient's breast on the imaging system for subsequent imaging. In one example, the breast liner 700 can be adhered to the patient's breast prior to approaching the image system. FIG. 7A illustrates a substantially rectangular liner 700, although any other shape (e.g., circular, oval, etc.) may be used as required or desired. The breast liner 700 enables the technologist to more easily position and align the patient's breast on the imaging system without any pinch points forming on the breast tissue from the imaging system. For example, the one or markers 704 may be aligned to one or more corresponding locations on the imaging system to enable positioning of the patient's breast. This increases the efficiency of the imaging procedure and the overall comfort of the patient.

In another example, a portion of the breast liner 700 may be removably attached to the imaging system to further assist in positioning of the patient's beast for imaging procedures. The adhesive layer 702 and/or the marker 704 may be radiolucent so that the breast liner 700 is partially or completely invisible in the x-ray image and image artifacts are reduced or eliminated. In other examples, the markers 704 may be radio-opaque such that x-ray imaging can assist in positioning the patient's breast. The breast liners 700 described herein may be used with the breast securement devices described above in FIGS. 2-6 to facilitate breast placement with respect to the device and/or image systems. In other examples, the breast liners 700 may be used with the breast compression system described above in FIGS. 1A and 1B to facilitate breast placement on the support platform. In both breast compression methods and breast stabilization methods, the markers 704 may be utilized to determine compression and/or stabilization forces. For example, by monitoring a change in marker position during the compression or stabilization procedure.

Additionally or alternatively, at least one marker 704 may correspond to a previously identified region of interest 706. That is, the breast liner 700 can be custom printed for the patient so that the technologist can more easily position the patient's breast and focus imaging towards a predetermined area, such as the region of interest 706. The region of interest 706 may be based on identified features of the beast tissue desirable for imaging, or may be based on breast tissue features previously imaged for further image investigation.

FIG. 7B is a top view of another breast liner 750. Similar to the breast liner 700 (shown in FIG. 7A), the breast liner 750 includes an adhesive liner 752 and at least one marker 754. In this example, however, the marker 754 is in a grid pattern so as to assist the technologist in aligning the patient's breast on the imaging system. It is appreciated that any other marker type (e.g., crosshatch, hash marks, etc.) may be used as required or desired.

Figure 8:
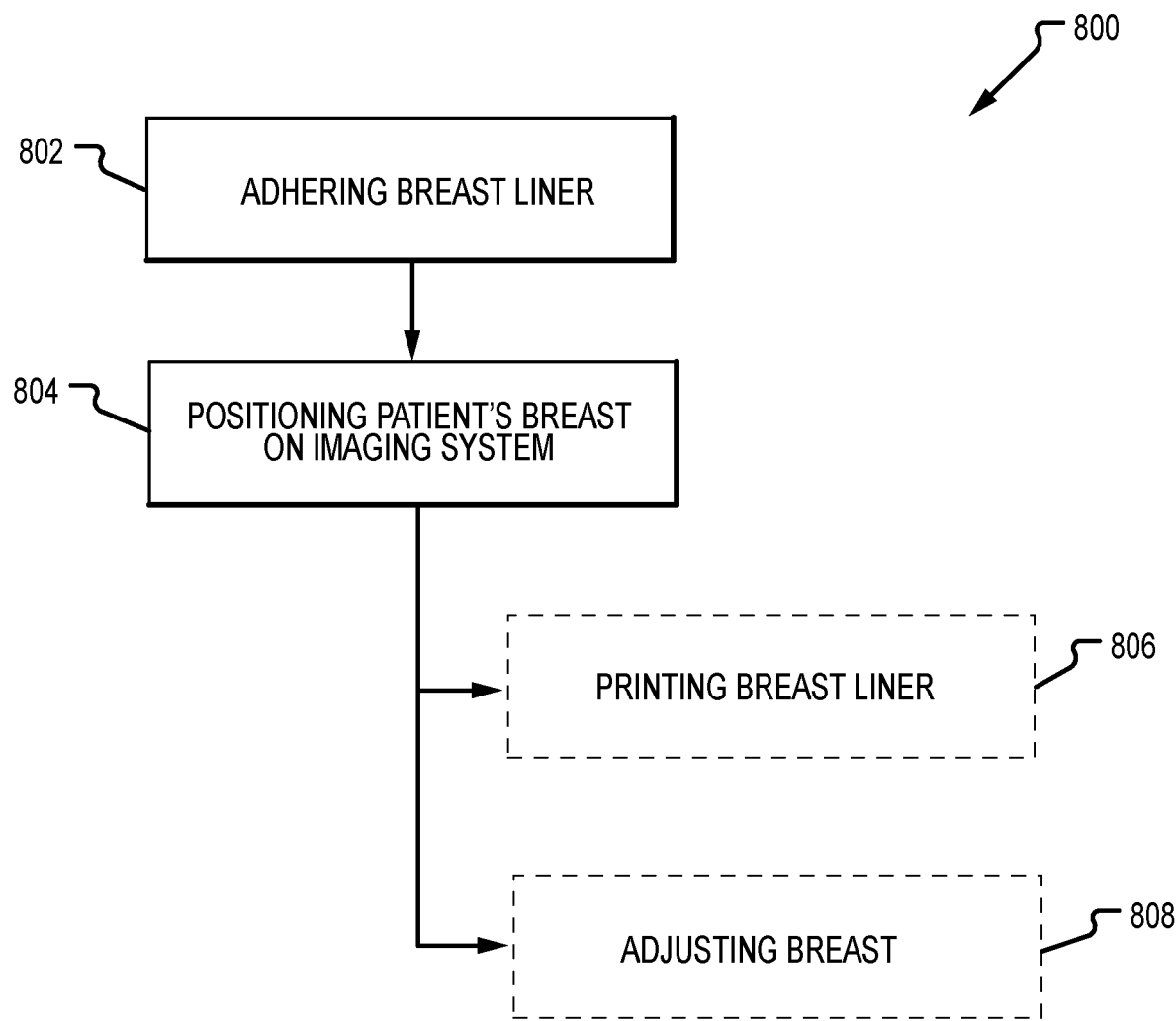
FIG. 8 is a flowchart illustrating a method of imaging a patient's breast.

FIG. 8 is a flowchart illustrating a method 800 of imaging a patient's breast in an imaging system. In the example, a breast liner is adhered to at least a portion of the patient's breast (operation 802). The breast liner can include at least one marker as described above in reference to FIGS. 7A and 7B. The patient's breast can then be positioned on the imaging system based at least in part by a location of the at least one marker relative to the imaging system (operation 804). This increases the efficiency of the imaging procedure and the overall comfort of the patient.

In some examples, the method 800 may further include printing the breast liner with the at least one marker corresponding to a previously identified region of interest (operation 806). This enables the breast liner to be customized and the patient's breast to be more easily positioned with the region of interest within the imaging area. In other examples, the method 800 may further include adjusting the patient's breast on the imaging system based on the at least one marker (operation 808). For example, the compression and/or stabilization force may be adjusted based on the location or change of location of the one or more markers.

Figure 9:
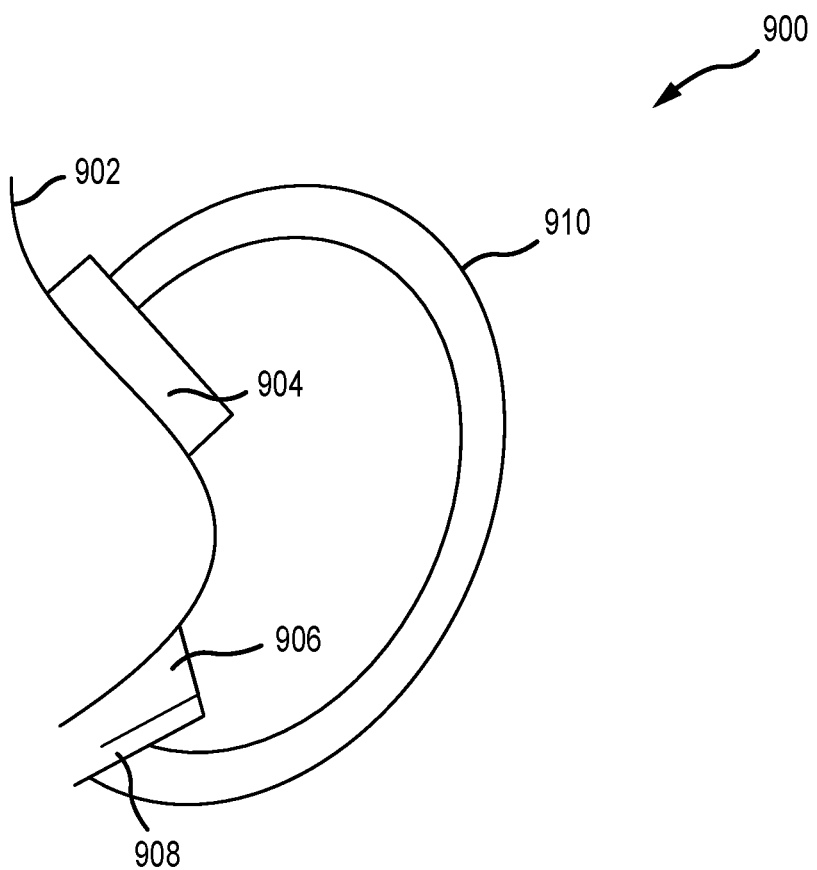
FIG. 9 is a schematic view of another imaging system.

FIG. 9 is a schematic view of another imaging system 900. In this example, the imaging system 900 includes a bra 902 configured to secure a patient's breast. The bra 902 is configured to stabilize and/or shape the patient's breast so that imaging can be performed while the patient is wearing the bra 902. As such, the bra 902 may be substantially radiolucent so that image artifacts are not formed in the resulting images. In some examples, at least a portion of the bra 902 may be an additively printed component (e.g., 3D printed) so that the bra 902 more closely corresponds to the size of the patient's breast. Additionally or alternatively, the bra 902 may shape the patient's breast such that the breast is shaped with bilateral symmetry. By using the bra 902 for stabilization and shape, the compression system described above in FIGS. 1A and 1B may be replaced and/or eliminated.

Once the patient's breast is stabilized and/or shaped, an imaging source 904 and a detector 906 may be selectively positionable relative to the bra 902 for imaging. The imaging source 904 may be an x-ray imager, an ultrasound imager, or any other imager as required or desired. In some example, the detector 906 may further include an intensifier 908 as required or desired. The imaging source 904 and the detector 906 are supported by an articulator 910 that is configured to position the imaging source 904 and/or the detector 906 at any location around the patient's breast. For example, based on the location of the bra 902, and thereby the patient's breast, the articulator 910 may sweep around the bra 902 for imaging. For example, a tomosynthesis sweep or a CT sweep may be performed. In other examples, the imaging source 904 and the detector 906 may be placed in CC or MLO mammography positions. The articulator 910, however, may position the imaging source 904 and the detector 906 at any other location as required or desired. For example, directing the imaging source 904 to a region of interest.

Figure 10:
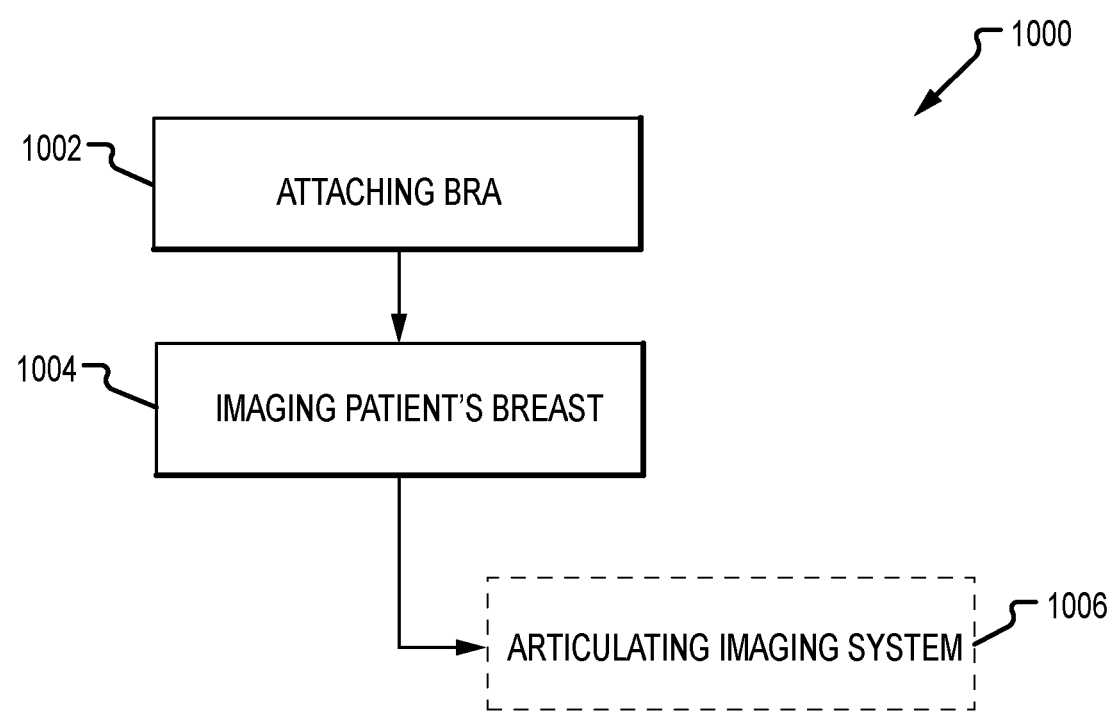
FIG. 10 is a flowchart illustrating a method of imaging a patient's breast.

FIG. 10 is a flowchart illustrating a method 1000 of imaging a patient's breast. In this example, the method 1000 begins with attaching a bra to a patent (operation 1002). For example, the radiolucent bra described above in FIG. 9 that stabilizes and/or shapes the patient's breast. Once the breast is secured, the patient's breast may be imaged via an imaging system that is selectively positionable relative to the bra (operation 1004). In some examples, the method 1000 may further articulate the imaging system to any location around the patient's breast (operation 1006). This articulation may be for tomosynthesis or CT sweeps, or any other movement as required or desired for the function of the imaging system as described herein.

This disclosure describes some examples of the present technology with reference to the accompanying drawings, in which only some of the possible examples were shown. Other aspects can, however, be embodied in many different forms and should not be construed as limited to the examples set forth herein. Rather, these examples were provided so that this disclosure was thorough and complete and fully conveyed the scope of the possible examples to those skilled in the art. Any number of the features of the different examples described herein may be combined into one single example and alternate examples having fewer than or more than all of the features herein described are possible. It is to be understood that terminology employed herein is used for the purpose of describing particular examples only and is not intended to be limiting. It must be noted that, as used in this specification, the singular forms "a," "an," and "the" include plural referents unless the context clearly dictates otherwise.

Although specific examples were described herein, the scope of the technology is not limited to those specific examples. One skilled in the art will recognize other examples or improvements that are within the scope of the present technology. Therefore, the specific structure, acts, or media are disclosed only as illustrative examples. Examples according to the technology may also combine elements or components of those that are disclosed in general but not expressly exemplified in combination, unless otherwise stated herein. The scope of the technology is defined by the following claims and any equivalents therein.

What is claimed is:

1. A breast securement device for an imaging system, the securement device comprising:
   a retainer configured to attach to at least a portion of a patient's breast, wherein the retainer comprises a bra comprising an adhesive member configured to adhere to the patient's breast; and
   a tensioning system removably coupled to the retainer, wherein the tensioning system is configured to pull the retainer away from a chest wall of a patient so as to apply a pulling force to the patient's breast.

2. The breast securement device of claim 1, wherein the retainer comprises one or more markers.

3. The breast securement device of claim 2, wherein the one or more markers are radiolucent.

4. The breast securement device of claim 2, wherein the one or more markers are radio-opaque.

5. The breast securement device of claim 2, wherein the one or more markers correspond to a region of interest.

6. The breast securement device of claim 2, wherein the one or more markers comprise a grid pattern.

7. The breast securement device of claim 1, wherein the adhesive member comprises a plurality of adhesive members.

8. The breast securement device of claim 7, wherein at least one of the plurality of adhesive members is positioned on a top of the patient's breast and at least one of the plurality of adhesive members is positioned on a bottom of the patient's breast.

9. The breast securement device of claim 1, wherein the adhesive member comprises a foam or a pad.

10. The breast securement device of claim 9, wherein the foam or the pad is configured to shape at least a portion of the patient's breast.

11. The breast securement device of claim 1, wherein the imaging system is an x-ray imaging system and the tensioning system is coupled to a support arm.

12. A method of securing a patient's breast for imaging, the method comprising:
    attaching a retainer to at least a portion of the patient's breast, wherein the retainer includes a bra attached to a patient including an adhesive member adhered to the patient's breast; and
    pulling the retainer away from a chest wall of the patient.

13. The method of claim 12, further comprising positioning the patient's breast on an imaging system based at least in part by a location of one or more markers disposed on the retainer relative to the imaging system.

14. The method of claim 12, further comprising coupling the retainer to a tensioning system.

15. The method of claim 12, wherein the adhesive member is positioned on a top and a bottom of the patient's breast.

16. The method of claim 12, wherein pulling the retainer stabilizes the patient's beast relative to an imaging system.

17. The method of claim 12, wherein the adhesive member includes a foam or a pad, and wherein the foam or the pad shapes at least a portion of the patient's breast.

\* \* \* \* \*